(12) United States Patent
Hawkes (10) Patent No.: US 9,327,041 B2
(45) Date of Patent: May 3, 2016

(54) MEDICAL INSTRUMENT STERILIZATION CONTAINER AND METHOD

(75) Inventor: Jason Hawkes, Weare, NH (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 1568 days.

(21) Appl. No.: 12/183,357

(22) Filed: Jul. 31, 2008

(65) Prior Publication Data
US 2009/0223964 A1    Sep. 10, 2009

Related U.S. Application Data

(60) Provisional application No. 61/033,819, filed on Mar. 5, 2008.

(51) Int. Cl.
*A61L 2/26* (2006.01)

(52) U.S. Cl.
CPC .............. *A61L 2/26* (2013.01); *A61L 2202/182* (2013.01)

(58) Field of Classification Search
USPC ....................................... 220/326; 292/10, 34
See application file for complete search history.

(56) References Cited

U.S. PATENT DOCUMENTS

| | | | | |
|---|---|---|---|---|
| 4,693,386 A * | 9/1987 | Hughes et al. | ................ | 220/1.5 |
| 4,781,407 A * | 11/1988 | Rauchhaus | ................... | 292/37 |
| 4,915,913 A * | 4/1990 | Williams et al. | ............ | 422/119 |
| 4,917,255 A * | 4/1990 | Foy et al. | ......................... | 220/6 |
| 4,923,079 A * | 5/1990 | Foy | ................................. | 220/7 |
| 5,161,709 A * | 11/1992 | Oestreich, Jr. | ................... | 220/6 |
| 5,199,592 A * | 4/1993 | Reiland et al. | ................ | 220/817 |
| 5,246,128 A * | 9/1993 | Uitz | ............................. | 220/4.28 |
| 5,285,900 A * | 2/1994 | Swingler | ....................... | 206/508 |
| 5,384,103 A * | 1/1995 | Miller | ............................. | 422/310 |
| 5,394,983 A | 3/1995 | Latulippe et al. | | |
| 5,411,136 A | 5/1995 | Brigham | | |
| 5,558,241 A * | 9/1996 | Huffstutler et al. | ............ | 220/1.5 |
| 5,597,084 A * | 1/1997 | Parasin | ........................ | 220/4.28 |
| 5,683,008 A * | 11/1997 | Galer | ......................... | 220/345.3 |
| 5,711,444 A * | 1/1998 | Meacham et al. | ................ | 220/6 |
| 5,843,387 A | 12/1998 | Dane et al. | | |
| 5,887,745 A | 3/1999 | Wood | | |
| 5,913,422 A | 6/1999 | Cote et al. | | |
| 6,116,452 A * | 9/2000 | Hamel et al. | ................... | 220/318 |
| 6,138,850 A * | 10/2000 | Berry, III | ..................... | 220/4.28 |
| 6,164,738 A * | 12/2000 | Dane et al. | ..................... | 312/311 |
| 6,293,418 B1 * | 9/2001 | Ogden et al. | ........................ | 220/7 |
| 6,484,898 B2 * | 11/2002 | Hillis et al. | ......................... | 220/6 |
| 6,585,942 B1 * | 7/2003 | Bussell et al. | ................ | 422/300 |
| 6,642,446 B2 * | 11/2003 | Dodds et al. | ..................... | 174/50 |
| 6,776,300 B2 * | 8/2004 | Walsh et al. | ........................ | 220/6 |

(Continued)

FOREIGN PATENT DOCUMENTS

WO    WO0249682 A1    6/2002

*Primary Examiner* — Fenn Mathew
(74) *Attorney, Agent, or Firm* — Hayes Soloway PC (57) ABSTRACT

The system contains a container, comprising a plurality of sides, each side having a plurality of fluid permeable openings, wherein the plurality of sides form a substantially enclosed unit. The system contains at least one lid. The system contains at least one latch unit for movably attached to a first side of the plurality of sides at a proximate end of the latch unit. The system contains a lid restraint, formed at a distal end of the latch unit whereby the lid restraint restrains the lid when engaged with the lid. Lastly, the system contains at least one locking element formed along the latch unit for engagement with the first side, wherein engagement of the locking element limits the mobility of the latch unit.

18 Claims, 13 Drawing Sheets

(56) References Cited

U.S. PATENT DOCUMENTS

| | | | |
|---|---|---|---|
| 7,357,271 B2* | 4/2008 | Hase et al. | 220/592.2 |
| 7,364,210 B2* | 4/2008 | Schainholz et al. | 292/307 A |
| RE41,323 E* | 5/2010 | Kellerer et al. | 220/7 |
| 7,784,631 B2* | 8/2010 | Winn et al. | 220/6 |
| 2003/0198581 A1* | 10/2003 | Sweet et al. | 422/292 |
| 2005/0178770 A1* | 8/2005 | Hase et al. | 220/592.2 |
| 2005/0224384 A1 | 10/2005 | Sands | |
| 2006/0144838 A1* | 7/2006 | Winn et al. | 220/7 |
| 2006/0213794 A1 | 9/2006 | Foreman | |
| 2006/0266666 A1* | 11/2006 | Bettenhausen et al. | 206/370 |
| 2009/0200307 A1* | 8/2009 | Giraud et al. | 220/326 |
| 2009/0223964 A1* | 9/2009 | Hawkes | 220/324 |
| 2010/0300910 A1* | 12/2010 | Hawkes | 206/363 |

* cited by examiner

FIG. 14 ical Instrument Sterilization Container and Method

Cross Reference to Related Application

This application claims benefit of U.S. Provisional Application Ser. No. 61/033,819 filed Mar. 5, 2008, the entire disclosure of which is incorporated herein by reference.

Field of the Invention

The present invention is generally related to containers, and more particularly is related to medical instrument sterilization containers.

Background of the Invention

Containers are utilized in a variety of industries for a variety of purposes, such as housing, storing and transporting products. Containers have evolved to include lids that can be removably attached to a container or moveably affixed to a container. This allows for convenient access and/or removal of a stored or transported product when one wishes to use the product. Lids that can be moveably affixed or removed from the container with greater efficiency and convenience are desired in commercial industries to save money and time. The medical instrument sterilization field is one such industry. Persons and companies within this industry desire sterilization containers that provide a more efficient and more convenient usage.

Thus, a heretofore unaddressed need exists in the industry to address the aforementioned deficiencies and inadequacies.

Summary of the Invention

Embodiments of the present invention provide a system and method for medical instrument sterilization containers. Briefly described, in architecture, one embodiment of the system, among others, can be implemented as follows. The system contains a container having a plurality of sides, each side having a plurality of fluid permeable openings, wherein the plurality of sides form a substantially enclosed unit. The system includes at least one lid. At least one latch unit is movably attached to a first side of the plurality of sides at a proximate end of the latch unit. A lid restraint is formed at a distal end of the latch unit whereby the lid restraint restrains the lid when engaged with the lid. At least one locking element formed along the latch unit engages the first side, wherein engagement of the locking element limits the mobility of the latch unit.

The present invention can also be viewed as providing a method for using medical instrument sterilization container. In this regard, one embodiment of such a method, among others, can be broadly summarized by the following steps: providing a container having an opening, a plurality of fluid permeable sides; a latch unit, moveably affixed to a first side of the plurality of fluid permeable sides; placing a lid over the opening of the container; moving the latch unit to a closed position; manipulating a locking mechanism within the latch unit to engage the first side; and engaging a lid restraint, integral with the latch unit, with the lid.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

Brief Description of the Drawings

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

Detailed Description

Figure 1:
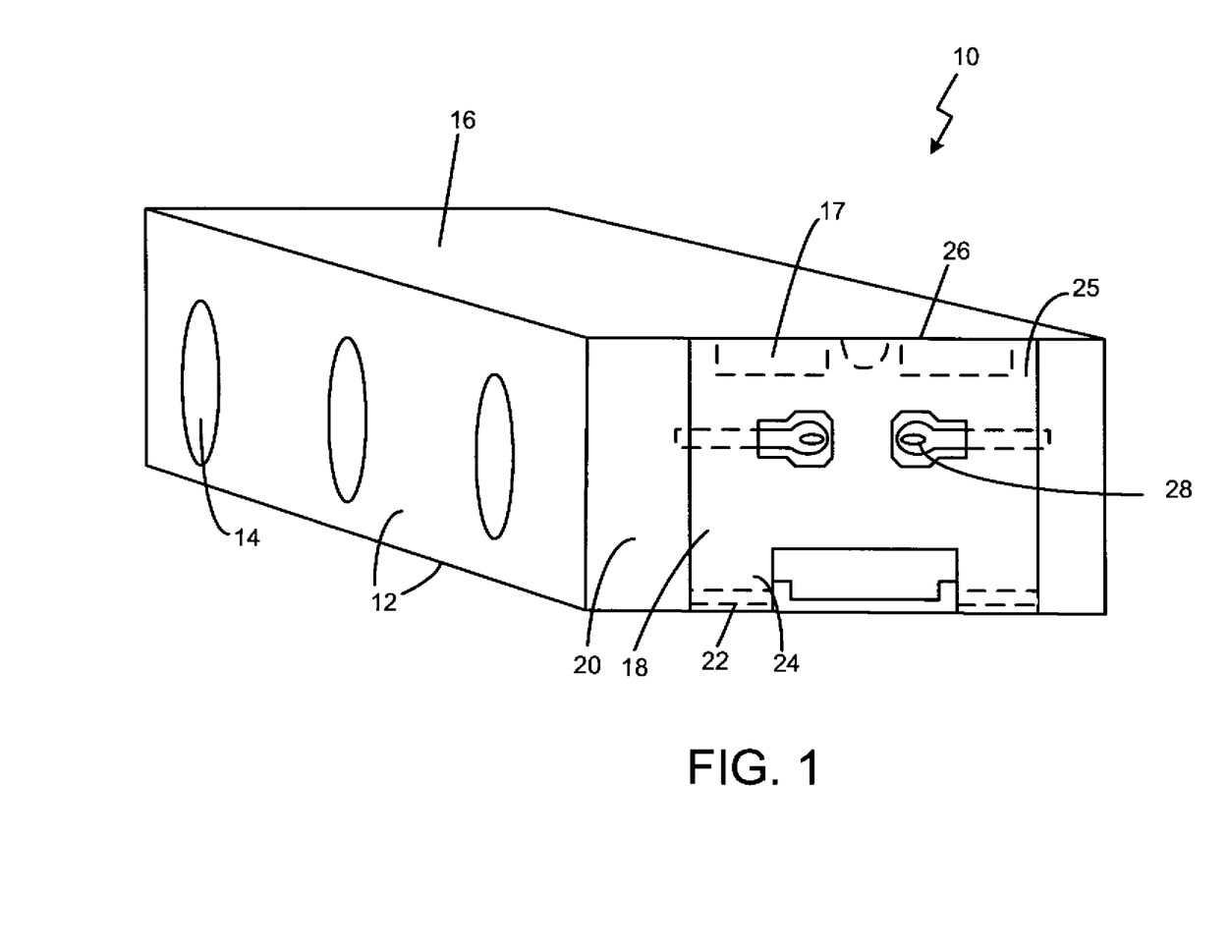
FIG. 1 is an illustration of a perspective view of a container in a closed position in accordance with a first exemplary embodiment of the present invention.

FIG. 1 is an illustration of a perspective view of a container 10 in a closed position, in accordance with a first exemplary embodiment of the present invention. The container 10 includes a plurality of sides 12. The sides 12 have a plurality of fluid permeable openings 14 which allow sterilization materials to enter the container 10 during a sterilizing process. A lid 16 is included with the container 10. The lid 16 includes a retainer area 17 integral with the lid 16 and disposed along at least one of the ends. A latch unit 18 is attached to a first side 20 of the container 10. In the first exemplary embodiment the latch unit 18 is attached to the first side 20 with a hinge 22, although other attachment devices may be similarly functional. The hinge 22 is located at a proximate end 24 of the latch unit 18. A lid restraint 26 is formed at a distal end 25 of the latch unit 18. When the latch unit 18 is in a closed position, as shown in FIG. 1, the lid restraint 26 mechanically engages the lid 16 and prevents the lid 16 from being removed. A locking element 28 is disposed within the latch unit 18. The locking element 28 is situated to engage the first side 20 of the container 10, which limits the mobility of the latch unit 18 and subsequently the lid 16. The latch unit 18 may include a plurality of locking elements 28.

One embodiment of the container 10 is a medical sterilization container. As such, the elements of the container 10 may be constructed of one or more materials that are durable when subjected to frequent sterilization and storage of sharp medical instruments and, further, do not pose a risk of contamination to medical instruments. Similarly, various shapes and sizes of fluid permeable openings 14 are known to those having ordinary skill in the art and variations on the sizes and shapes of fluid permeable openings 14 shown herein are considered to be within the scope of the present invention. The lid 16 and latch unit 18 may be made of the same material as the sides 12 or may be made of a different material. While the latch unit 18 is shown to be located on a first side 20 that is narrower than some of the other sides of the container 10, the latch unit 18 can functionally be at least partially located on any side 12 that may abut the lid 16.

Figure 2:
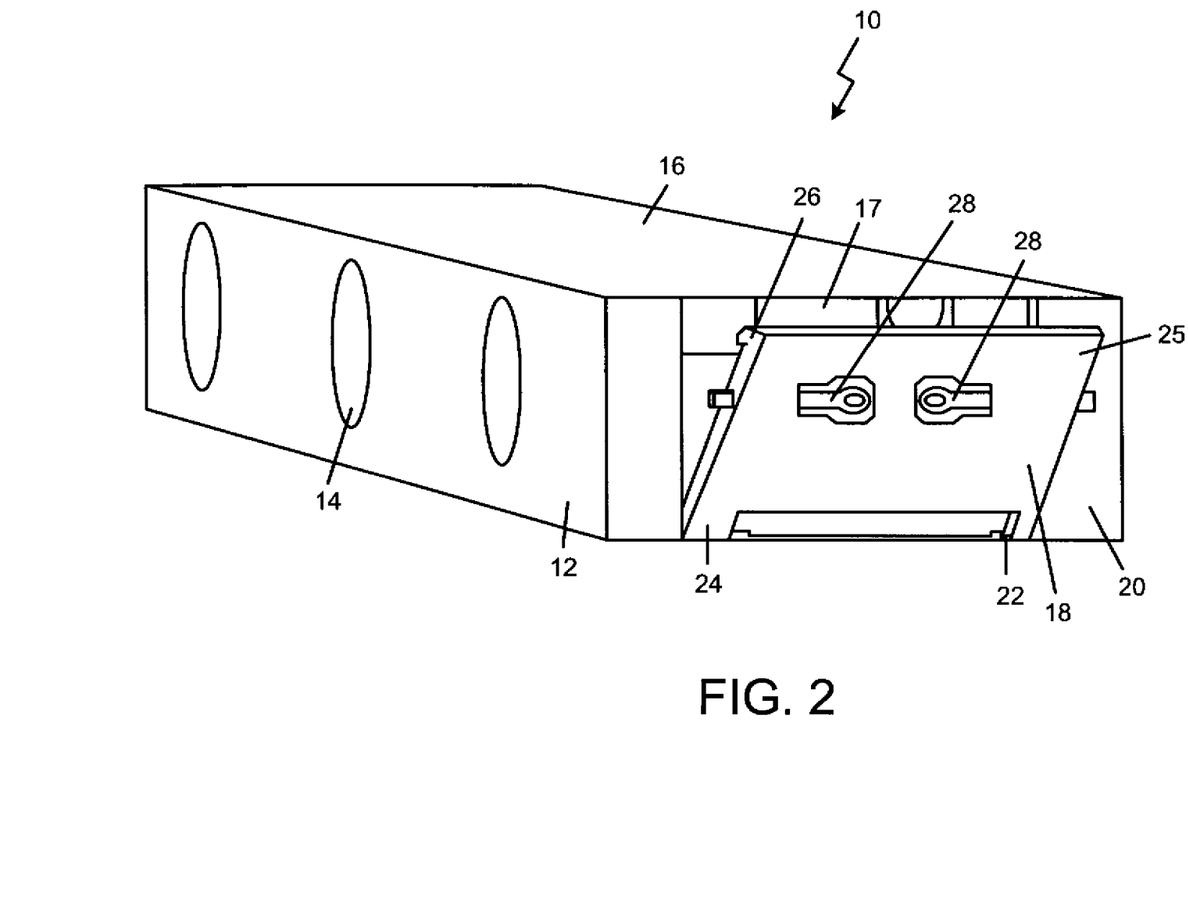
FIG. 2 is an illustration of the container of FIG. 1 in an open position, in accordance with a first exemplary embodiment of the present invention.

FIG. 2 is an illustration of the container 10 of FIG. 1 in an open position, in accordance with a first exemplary embodiment of the present invention. When the latch unit 18 is in an open position, the lid restraint 26 does not engage with the lid 16 and the lid 16 can be removed from the container 10 by a user. While the latch unit 18 is shown in the first exemplary embodiment occupying a substantial portion of the first side 20 of the container 10, other shapes and dimensions may be adopted for the latch unit 18 without departing from the scope of the present invention.

Figure 3:
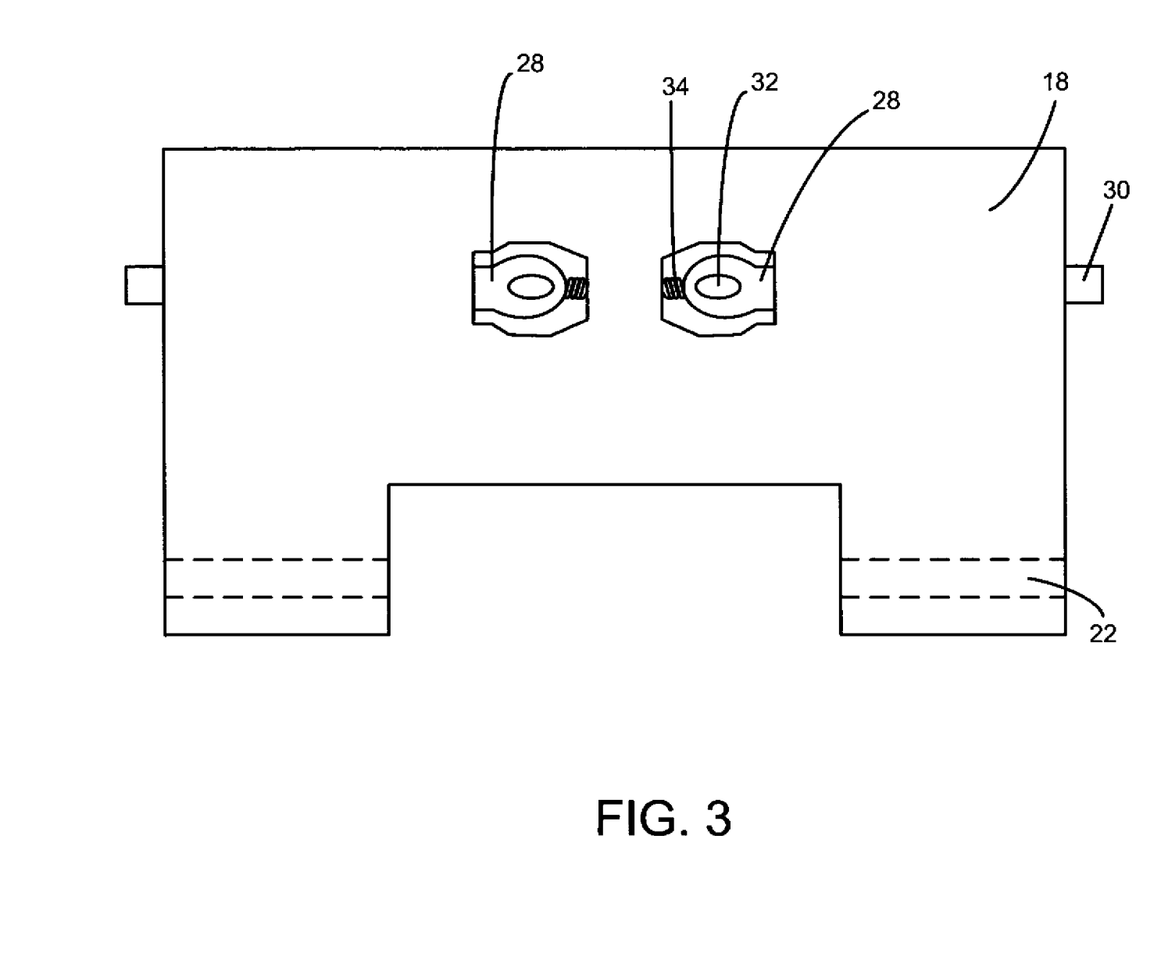
FIG. 3 is an illustration of a front view of a latch unit of the container in FIG. 1, in accordance with the first exemplary embodiment of the present invention.

FIG. 3 is an illustration of a front view of a latch unit 18 of the container 10 in FIG. 1, in accordance with the first exemplary embodiment of the present invention. The latch unit 18 may include one locking element 28 or a plurality of locking elements 28. The locking elements 28, in the first exemplary embodiment, may include a male connector 30 that is integral with a human manipulation area 32 and slidably oriented to the latch unit 18. A biasing mechanism 34 may be in mechanical communication with the locking element 28. The biasing mechanism 34 may bias the locking element 28 in a direction along which it is slidable. More specifically, the biasing mechanism 34 may bias the locking element 28 in a locked position, which is shown in FIG. 3, wherein the locking element 28 may be engaged to move the latch unit 18 between the closed position and the open position.

Figure 4:
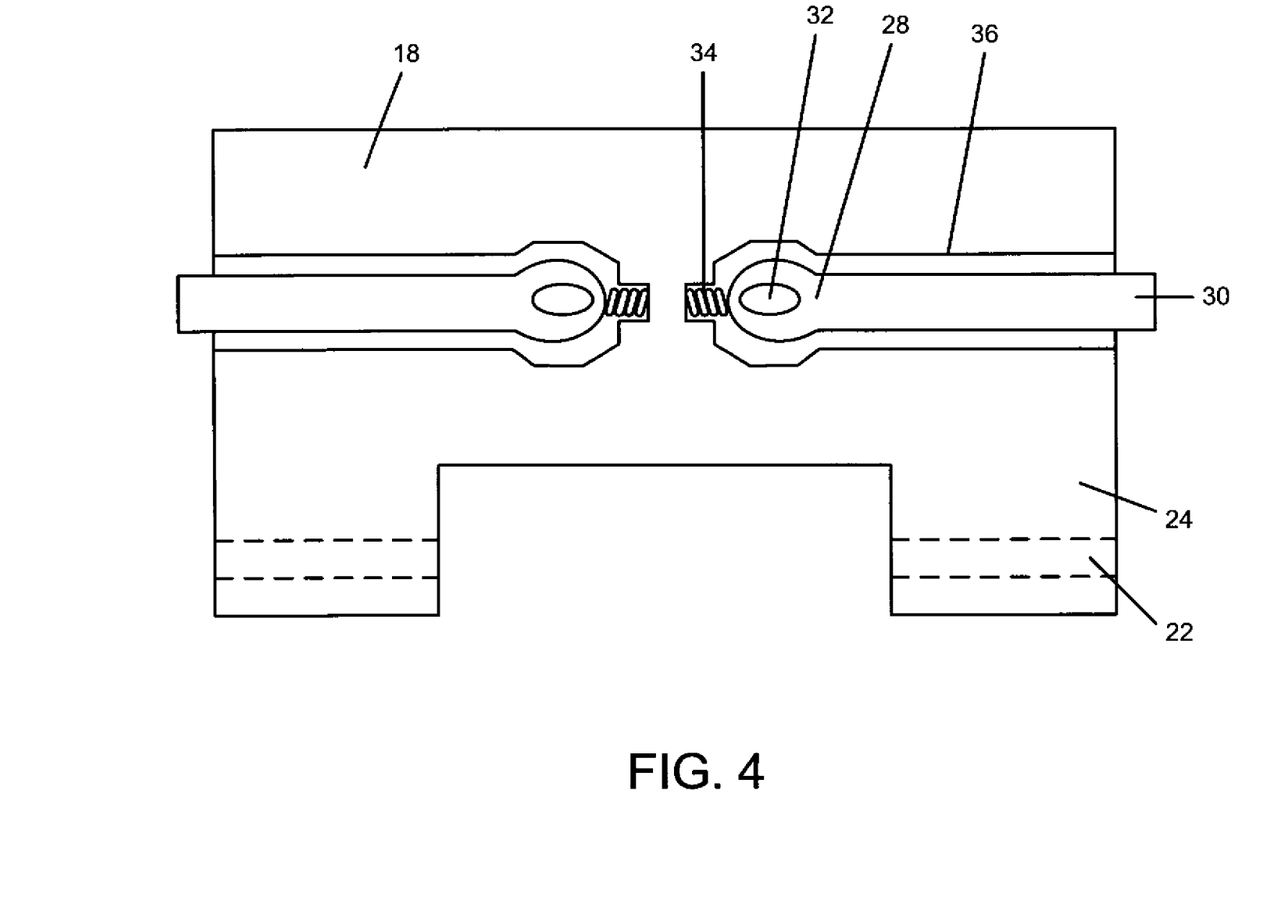
FIG. 4 is an illustration of a rear view of the latch unit of the container in FIG. 1, in accordance with the first exemplary embodiment of the present invention.

FIG. 4 is an illustration of a rear view of the latch unit 18 of the container 10 in FIG. 1, in accordance with the first exemplary embodiment of the present invention. In the first exemplary embodiment, the biasing mechanism 34 is shown to be a spring. The biasing mechanism 34 may be any device known to those having ordinary skill in the art to be capable of biasing the locking element 28, including but not limited to a spring, an inflatable capsule, a flexible material and a compressible material. The biasing mechanism 34 is in mechanical communication with the locking element 28, which includes a human manipulation area 32 and a male connector 30. The male connector 30 may be situated within a guide system 36 integral with the latch unit 18. The end of the male connector 30 may be designed for efficient engagement with a female connector 38 (shown in FIG. 5). The guide system 36 may guide the movement of the locking element 28 and prevent the locking element 28 from being over-biased by the biasing mechanism 34. The human manipulation area 32 of the locking element 28 may be designed for easy ergonomic use.

As seen in FIG. 4, a plurality of locking elements 28 may be disposed within a latch unit 18. The locking elements 28 may be disposed symmetrically opposite from each other. A biasing mechanism 34 may be situated between the locking elements 28. The biasing mechanism 34 may be a compression-tension device which applies a force on the locking elements 28 within the latch unit 18.

Figure 5:
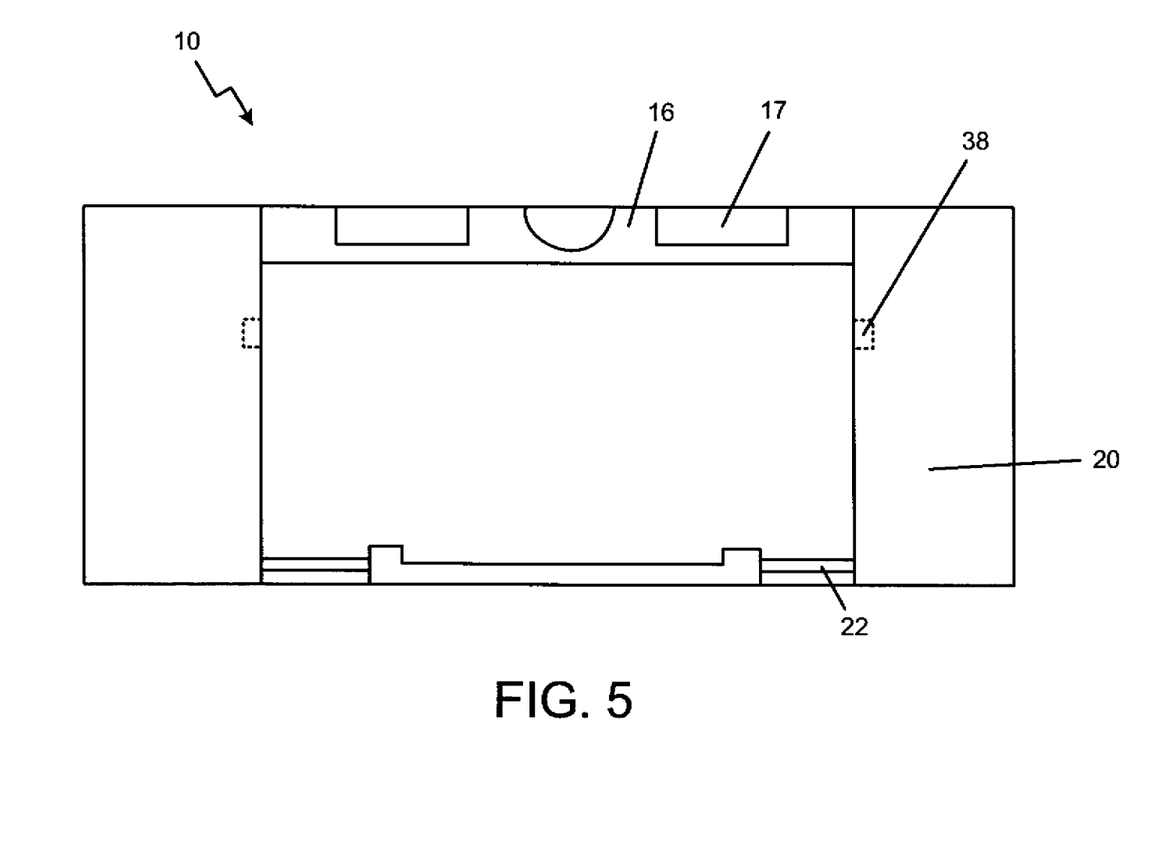
FIG. 5 is an illustration of a front view of the container without the latch unit of the container in FIG. 1, in accordance with the first exemplary embodiment of the present invention.

FIG. 5 is an illustration of a front view of the container 10 without the latch unit 18 of the container 10 in FIG. 1, in accordance with the first exemplary embodiment of the present invention. The proximate end 24 (shown in FIG. 4) of the latch unit 18 (shown in FIG. 4) may include a hinge 22 to pivot the latch unit 18 to and from the first side 20 of the container 10. When the latch unit 18 is pivoted toward the first side 20, the male connectors 30 (shown in FIG. 4) may engage the female connectors 38.

Figure 6:
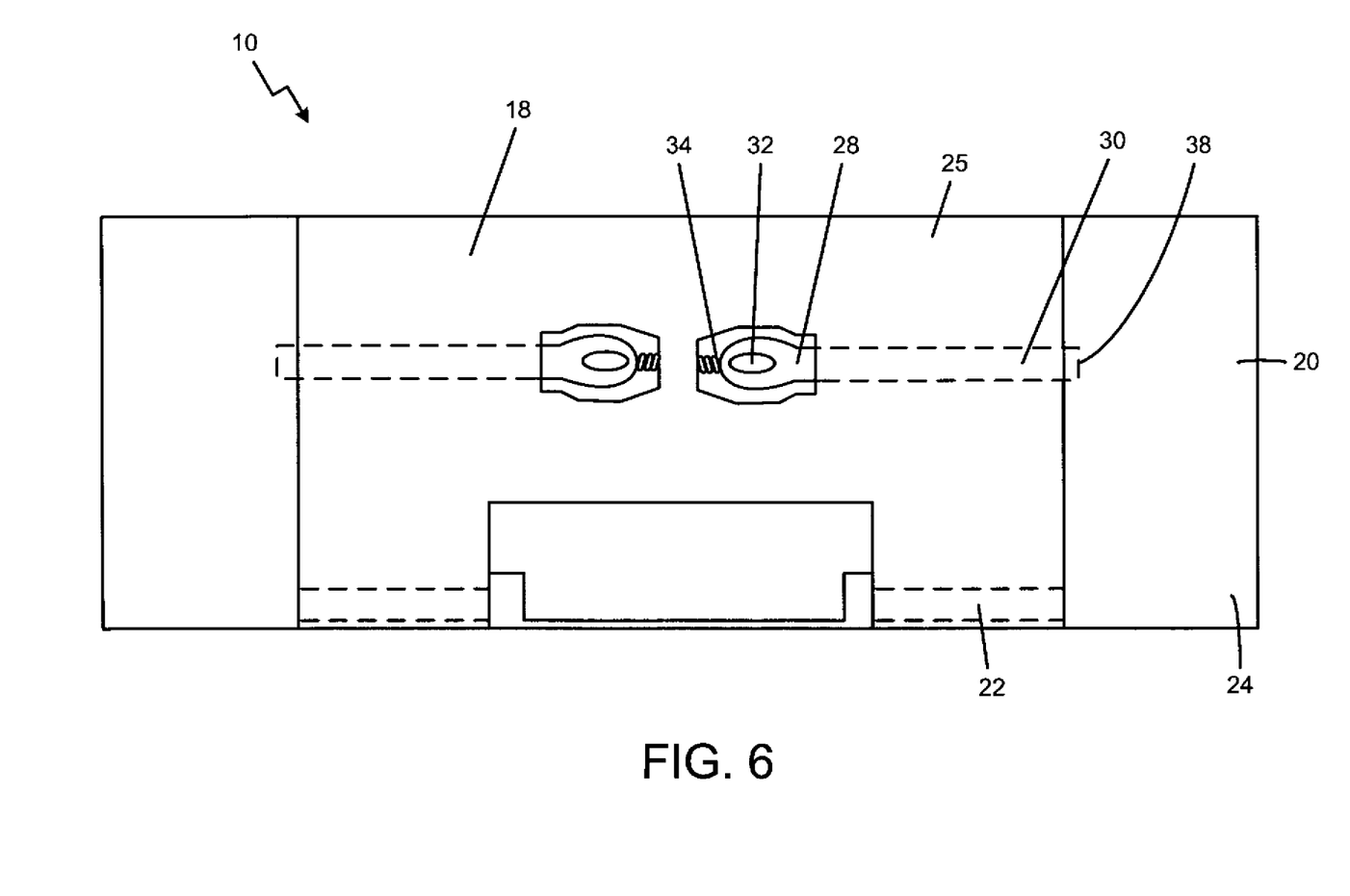
FIG. 6 is an illustration of a front view of the container in FIG. 1, in accordance with the first exemplary embodiment of the present invention.

FIG. 6 is an illustration of a front view of the container 10 shown in FIG. 1, in accordance with the first exemplary embodiment of the present invention. Starting from the closed position, (which was shown in FIG. 1) a user may manipulate the locking elements 28 by pinching the human manipulation areas 32 with fingers. The locking elements 28 may be compressed towards each other, which will pull the male connectors 30 from the female connectors 38. The latch unit 18 may then be pivoted away from the container 10. The distal end 25 of the latch unit 18 is moved away from the first side 20 which will pivot the latch unit 18 about the hinge 22. This movement will disengage the lid retainer 26 (shown in FIG. 7) from the retainer area 17 (shown in FIG. 5) of the lid 16 (shown in FIG. 5), thereby allowing the lid 16 to be moved.

Starting from the open position, (as shown in FIG. 2) the lid 16 may be placed in communication with the container 10. The latch unit 18 is rotated about its proximate end 24 on the hinge 22. The male connectors 30 will come in communication with the first side 20 of the container 10. The user may compress the locking elements 28 against the biasing mechanism 34, thereby allowing the latch unit 18 to be placed in the closed position. Then a user may release the compression of the locking elements 28 such that the male connectors 30 extend into an adjacent female connector 38, integral with the first side 20 of the container 10. The male connectors 30 may be beveled to allow the closing motion of the latch unit 18 to press the male connectors 30 against an exterior surface of the first side 20 and mechanically urge the locking elements 28 into a compressed state such that the latch unit 18 becomes fully closed and the male connectors 30 engage the female connectors 38 without user interaction with the human manipulation areas 32.

Figure 7:
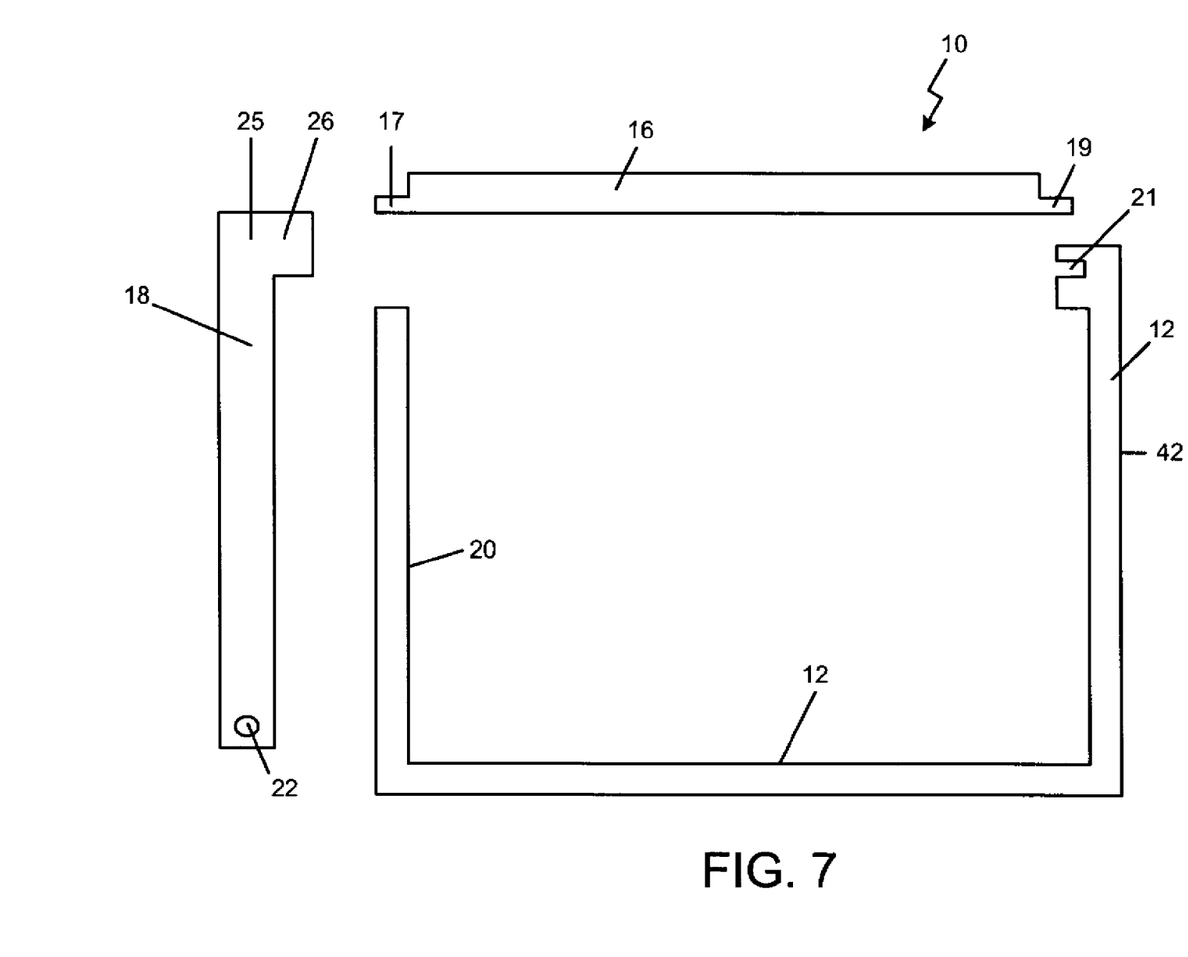
FIG. 7 is an illustration of an exploded cross-sectional side view of the container in FIG. 1, in accordance with the first exemplary embodiment of the present invention.

FIG. 7 is an illustration of an exploded cross-sectional side view of the container 10 with the latch unit 18 in FIG. 1, in accordance with the first exemplary embodiment of the present invention. The latch unit 18 has a lid retainer 26 located at the distal end 25 of the latch unit 18. The lid retainer 26 engages with the retaining area 17 of the lid 16 when the latch unit 18 is in the closed position (such as that shown in FIG. 1) and the lid 16 is on the container 10. The retaining area 17 may have a shape complimentary to and conforming with the lid retainer 26. The lid 16 may be part or all of a side 12 of the container 10. The lid 16 may have a retaining area 17 located on an end of the lid 16 that engages with the lid restraint 26 of the latch unit 18. The lid 16 will be prevented from opening when the lid restraint 26 is engaged with the restraining area 17 of the lid 16. An opposing side of the lid 16 may have an attachment mechanism 19, which engages with an attachment mechanism receiver 21 on a second side 42 of the plurality of sides 12 to keep the lid 16 secured. The attachment mechanism 19 and the attachment mechanism receiver 21 may be comprised of any form of attachment known to those having ordinary skill in the art and capable of restraining the opposing side of the lid 16 to the second side of the plurality of sides 12.

Figure 8:
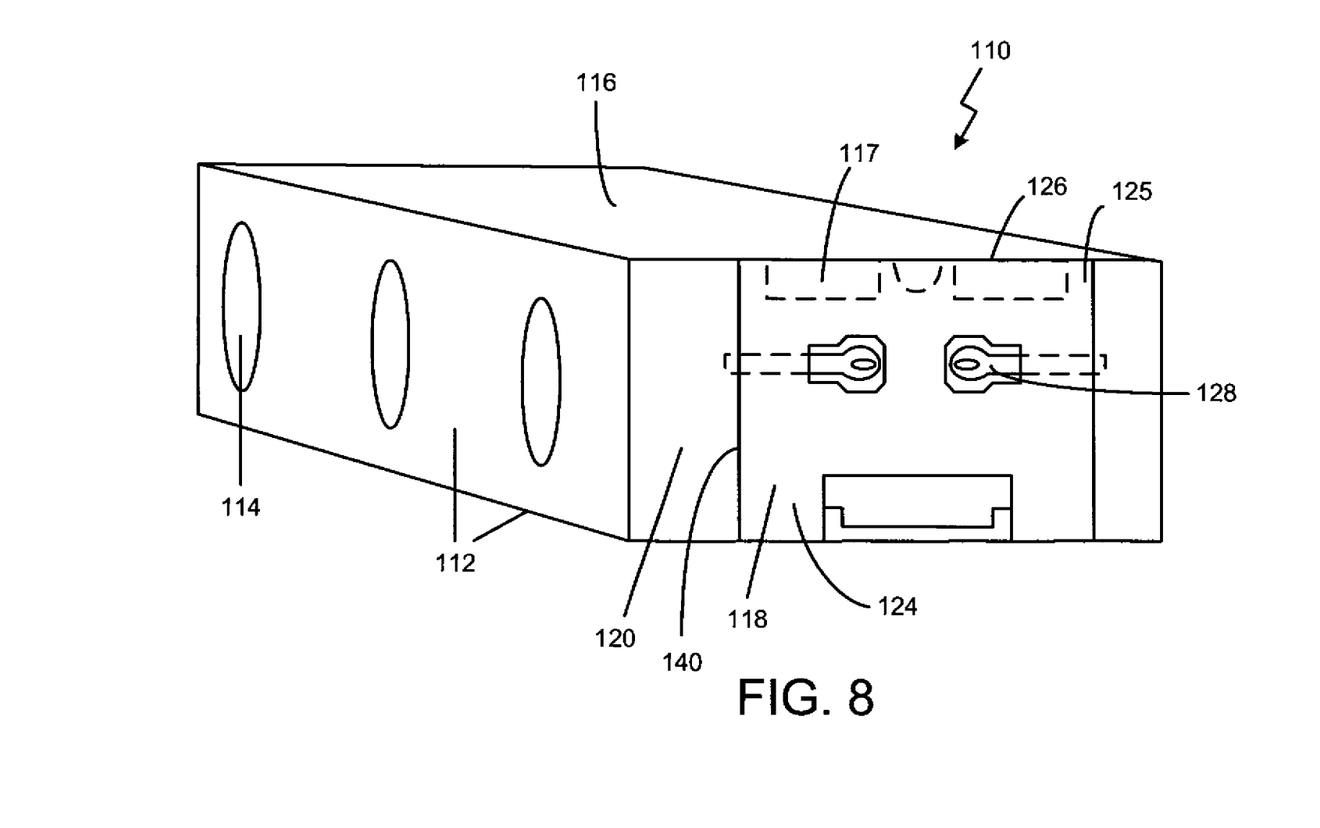
FIG. 8 is an illustration of a perspective view of a container in a closed position, in accordance with a second exemplary embodiment of the present invention.

FIG. 8 is an illustration of a perspective view of a container 110 in a closed position, in accordance with a second exemplary embodiment of the present invention. The container 110 includes a plurality of sides 112. The sides 112 have a plurality of fluid permeable openings 114 which allow sterilization materials to enter the container 110 during a sterilizing process. A lid 116 is included with the container 110. The lid 116 includes a retainer area 117 integral with the lid 116 and disposed along at least one of the ends. A latch unit 118 is attached to a first side 120 of the container 110. In the second exemplary embodiment the latch unit 118 is slidably attached to the first side 120 with a sliding mechanism 140, although other attachment devices may be similarly functional. A lid restraint 126 is formed at a distal end 125 of the latch unit 118. When the latch unit 118 is in a closed position the lid restraint 126 mechanically engages the lid 116 and prevents the lid 116 from being removed. A locking element 128 is disposed within the latch unit 118. The locking element 128 is situated to engage the first side 120 of the container 110, which limits the mobility of the latch unit 118 and subsequently the lid 116. The latch unit 118 may include a plurality of locking elements 128.

Figure 9:
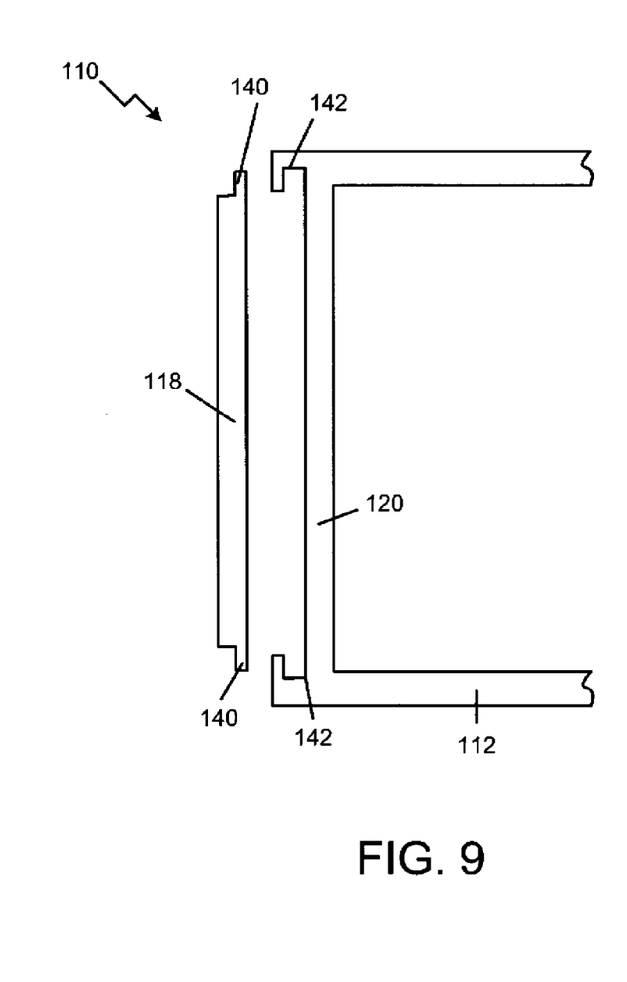
FIG. 9 is an illustration of an exploded cross-sectional top view of the container in FIG. 8, in accordance with the second exemplary embodiment of the present invention.

FIG. 9 is an illustration of an exploded cross-sectional top view of the container 110 in FIG. 8, in accordance with the second exemplary embodiment of the present invention. The latch unit 118 may be slidably attached to the first side 120 of the container 110 with a sliding mechanism 140. The sliding mechanism 140 may engage with a sliding mechanism receiver 142, integral with the first side 120 of the container 110. The sliding mechanism 140 may have a shape complimentary to and conforming with the sliding mechanism receiver 142, and may be comprised of any design known to those having ordinary skill in the art and capable of restraining the latch unit 118 to the first 120 side of the plurality of sides 112.

Figure 10:
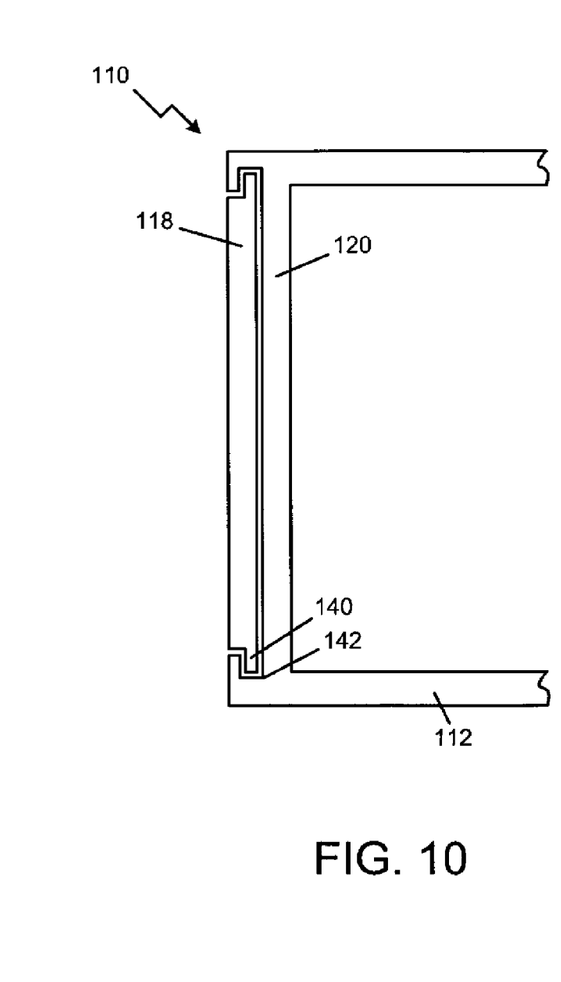
FIG. 10 is an illustration of a cross-sectional top view of the container in FIG. 8 in accordance with the second exemplary embodiment of the present invention.

FIG. 10 is an illustration of a top view of the container 110 in FIG. 8, in accordance with the second exemplary embodiment of the present invention. The latch unit 118 is attached to the first side 120 of the container 110 with a sliding mechanism 140. The sliding mechanism 140 of the latch unit 118 is engaged with the sliding mechanism receiver 142, integral with the first side 120 of the container 110. In accordance with this embodiment, engagement of the sliding mechanism 140 and the sliding mechanism receiver 142 restrains the latch unit 118 to abut the first side 120 when in the closed position (shown in FIG. 8). However, the sliding mechanism 140 and the sliding mechanism receiver 142 allow for movement of the latch unit 118 in a vertical direction, with respect to the first side 120 of the container 110. When the latch unit 118 is in the closed position, the locking mechanism 128 (FIG. 8) may be engaged with the first side 120 of the container 110, thereby restricting the vertical movement of the latch unit 118. When the locking mechanism 128 is disengaged from the first side 120 of the container 110, the latch unit 118 may be moved vertically. This movement may disengage the lid restraint 126 from the lid restraining area 117 of the lid 116 allowing the container 110 to be opened. One having ordinary skill in the art will recognize other available designs to the sliding mechanism 140 and the sliding mechanism receiver 142 to allow for directional variant movement. The latch unit 118 and the container 110 may include a plurality of sliding mechanisms 140 and sliding mechanism receivers 142, respectively. Further, the latch unit 118 and/or first side 120 may include a stop (not shown) to restrict a slidable range of the latch unit 118 and first side 120 to avoid full disengagement of the latch unit 118 from the container 110.

Figure 11:
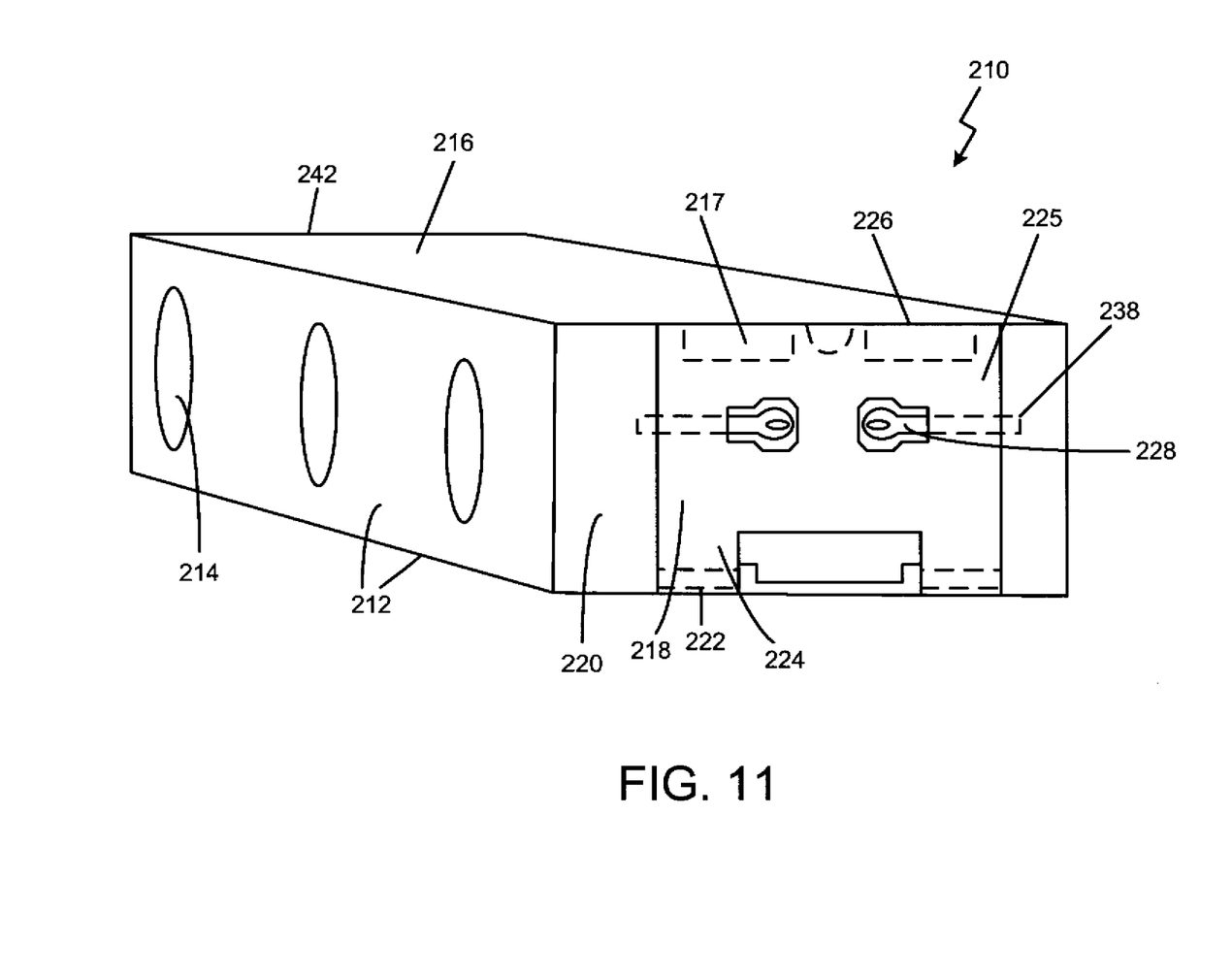
FIG. 11 is an illustration of a perspective view of a container in a closed position, in accordance with a third exemplary embodiment of the present invention.

FIG. 11 is an illustration of a perspective view of a container 210 in a closed position, in accordance with a third exemplary embodiment of the present invention. The container 210 includes a plurality of sides 212. The sides 212 have a plurality of fluid permeable openings 214 which allow sterilization materials to enter the container 210 during a sterilization process. A lid 216 is included with the container 210. The lid 216 includes a retainer area 217 integral with the lid 216 and disposed along at least one of the ends. A latch unit 218 is attached to a first side 220 of the container 210. In the third exemplary embodiment the latch unit 218 is attached to the first side 220 with a hinge 222, although other attachment devices may be similarly functional. The hinge 222 is located at a proximate end 224 of the latch unit 218. A lid restraint 226 is formed at a distal end 225 of the latch unit 218. When the latch unit 218 is in a closed position the lid restraint 226 mechanically engages the lid 216 and prevents the lid 216 from being removed. A locking element 228 is disposed within the latch unit 218. The locking element 228 is situated to engage the first side 220 of the container 210, which limits the mobility of the latch unit 218 and subsequently the lid 216. The latch unit 218 may include a plurality of locking elements 228. The latch units 218 may include a locking mechanism 228 comprising a male connector 230 that engages with a female connector 238 integral with the first side 220 and a second side 242.

Figure 12:
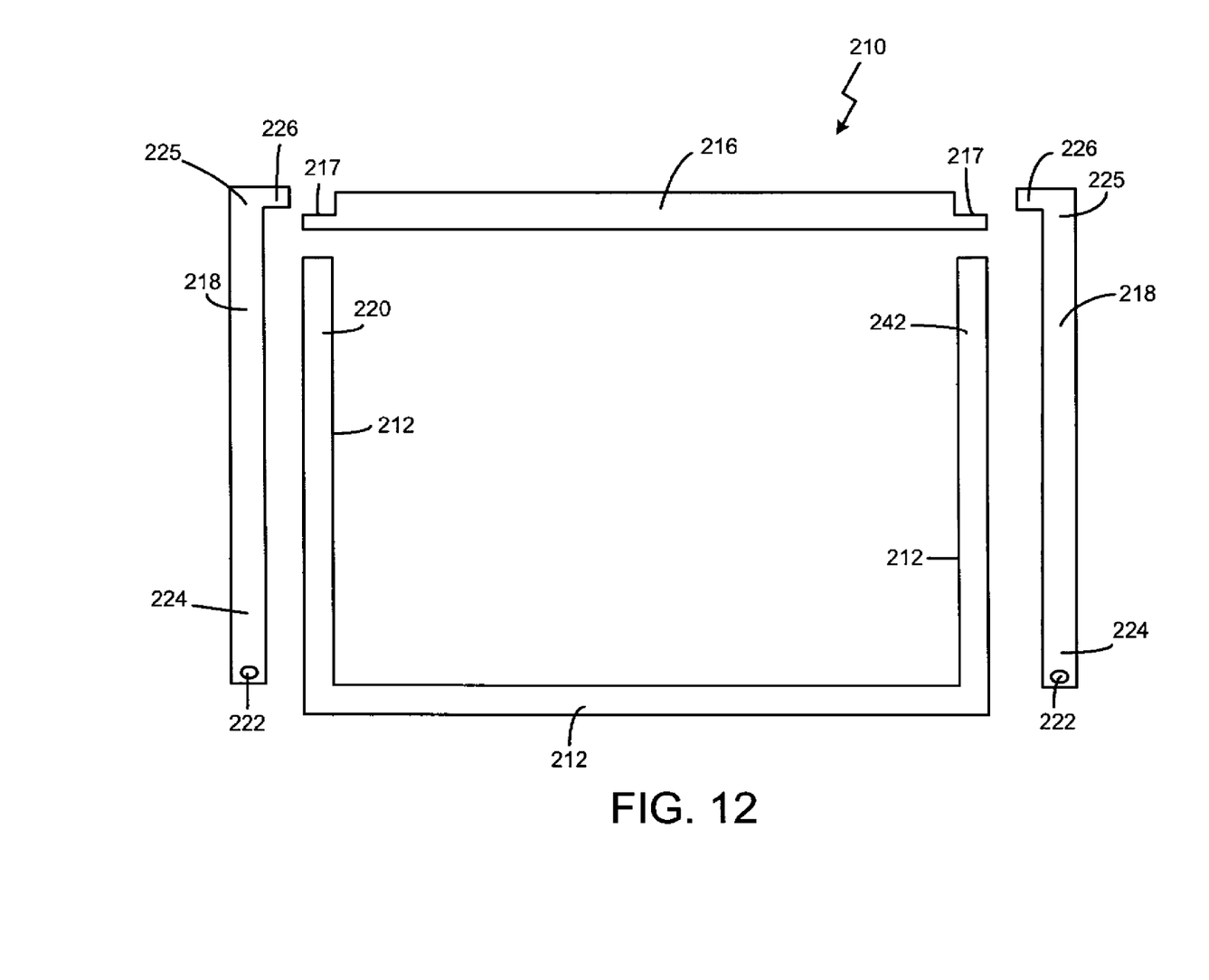
FIG. 12 is an illustration of an exploded cross-sectional side view of the container of FIG. 11, in accordance with the third exemplary embodiment of the present invention.

FIG. 12 is an illustration of an exploded cross-sectional side view of the container 210 in FIG. 11, in accordance with the third exemplary embodiment of the present invention. The container 210 includes the plurality of sides 212 and at least two latch units 218. The latch units 218 may be located at opposing ends of the container 210 and are situated to secure the lid 216 when in the closed position. The latch units 218 have lid restraints 226 formed at a distal end 225 of the latch units 218. The latch units 218 may also have a hinge 222 located at a proximate end 224 of the latch unit 218. The lid 216 may have a plurality of retaining areas 217 located at opposing ends of the lid 216 situated to engage with the lid restraints 226 of the latch units 218. A user may compress the locking mechanisms 228 (FIG. 11) in each of the latch units 218 to release the latch units 218 from the first side 220 and the second side 242 to release the lid 216 from the closed position.

Figure 13:
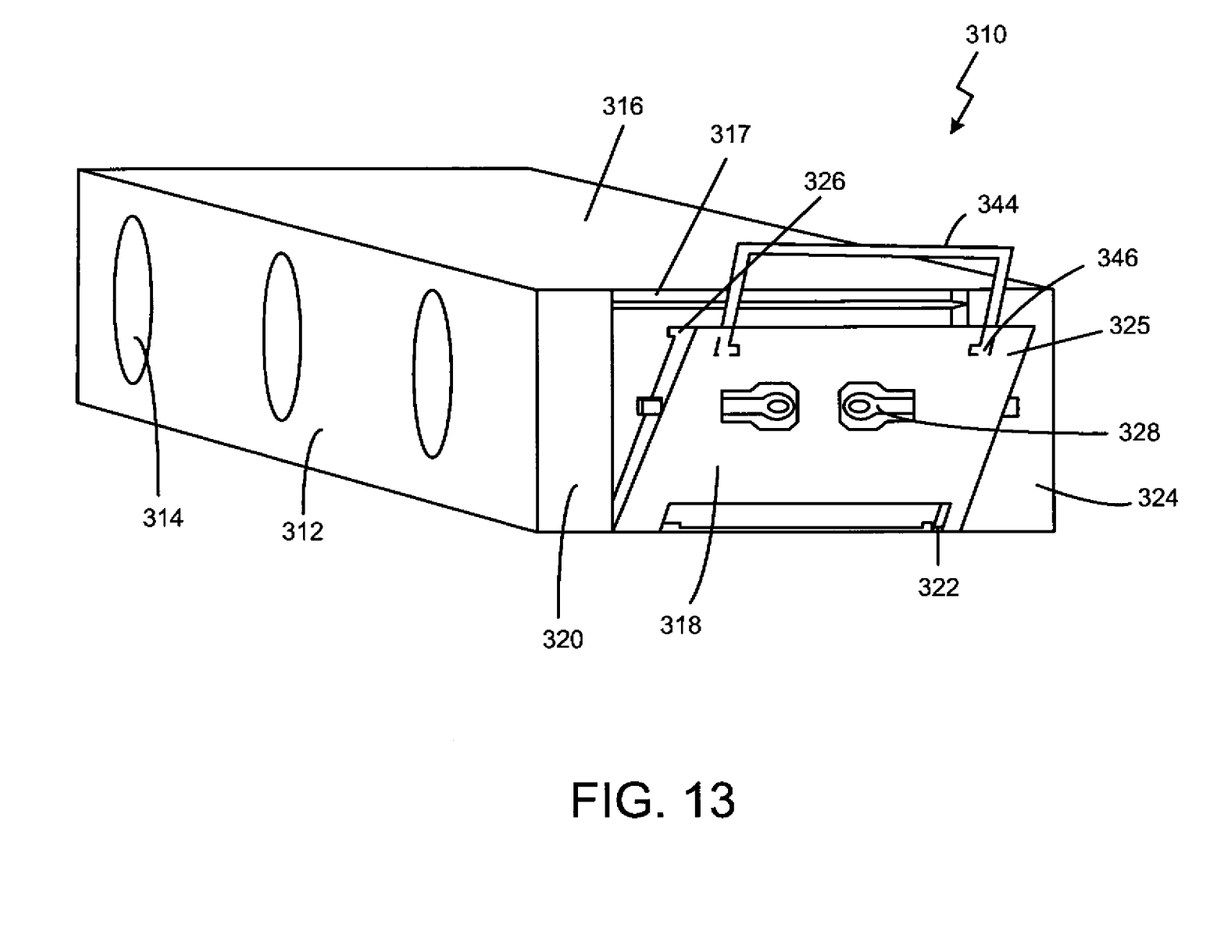
FIG. 13 is an illustration of a perspective view of a container, in accordance with a fourth exemplary embodiment of the present invention.

FIG. 13 is an illustration of a perspective view of a container 310 in an open position, in accordance with a fourth exemplary embodiment of the present invention. The container 310 includes a plurality of sides 312. The sides 312 have a plurality of fluid permeable openings 314 which allow sterilization materials to enter the container 310 during a sterilizing process. A lid 316 is included with the container 310. The lid 316 includes a retainer area 317 integral with the lid 316 and disposed along at least one of the ends. A latch unit 318 is attached to a first side 320 of the container 310 with a hinge 322, although other attachment devices may be similarly functional. A lid restraint 326 is formed at a distal end 325 of the latch unit 318. When the latch unit 318 is in a closed position the lid restraint 326 mechanically engages the retainer area 317 of the lid 316 and prevents the lid 316 from being removed. A locking element 328 is disposed within the latch unit 318. The locking element 328 is situated to engage the first side 320 of the container 310, which limits the mobility of the latch unit 318 and subsequently the lid 316. The latch unit 318 may include a plurality of locking elements 328.

A handle 344 may be included with the latch unit 318. The handle 344 may be partially disposed inside the latch unit 318 and retractable to allow for efficient use of space surrounding the container 310. The handle 344 may have a restraining device 346 to engage with the latch unit 318 and prevent the handle 344 from being completely removed from the latch unit 318. The handle 344 may be retractable into the interior of the latch unit 318 when the handle 344 is not being used. A handle 344 may also be used with a plurality of latch units 318. Those having skill in the art will recognize that other handle restraining devices 346 of similar functionality may be used. The handle 344 may be constructed of one or more materials that are durable when subjected to the forces of moving the container 310. The handle 344 may be designed for easy ergonomic use, allowing a user to conveniently move the container 310 from one location to another.

Figure 14:
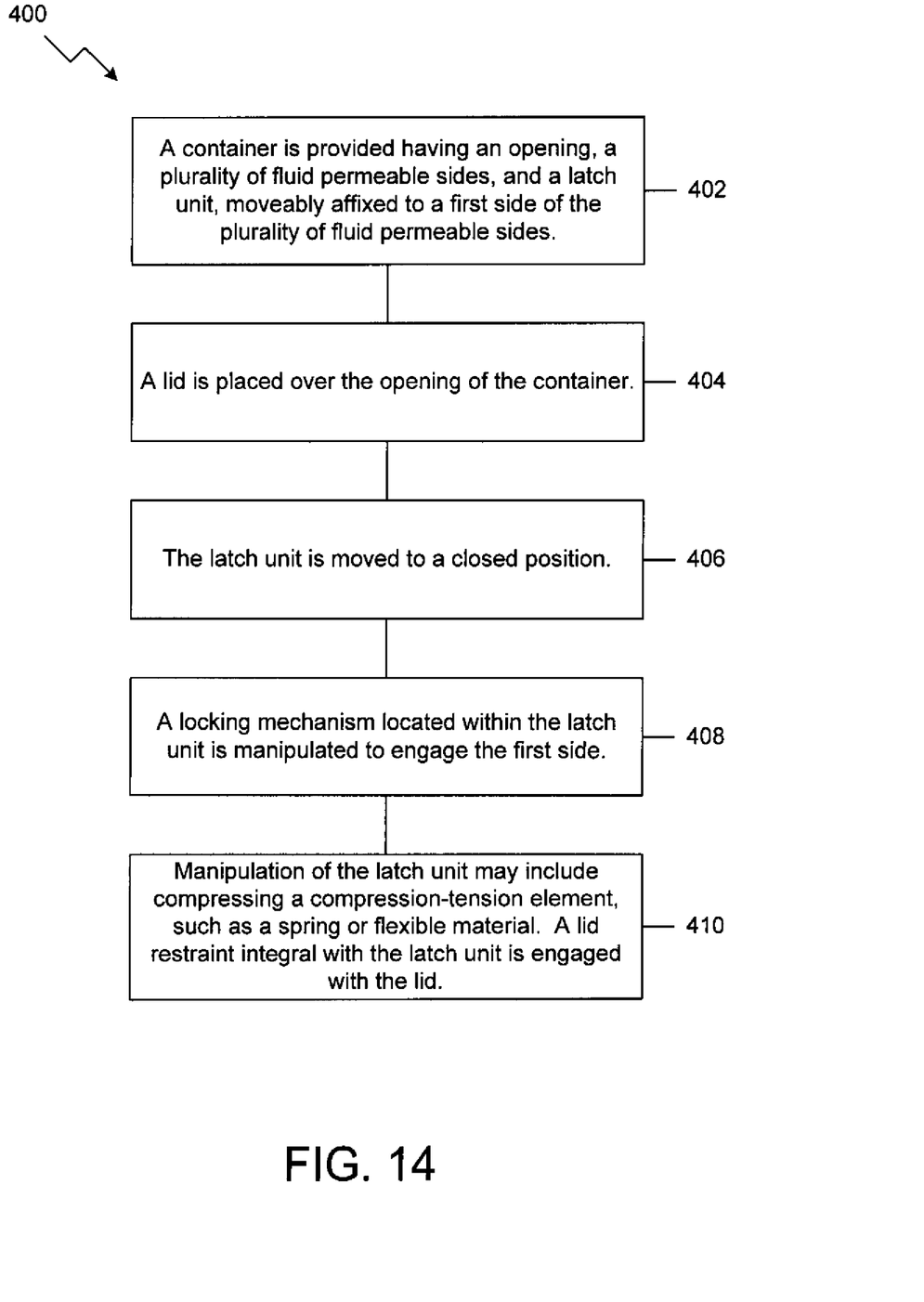
FIG. 14 is a flowchart illustrating a method of utilizing the container shown in FIG. 1, in accordance with the first exemplary embodiment of the present invention.

FIG. 14 is a flowchart 400 illustrating a method of utilizing the container 10 shown in FIG. 1, in accordance with the first exemplary embodiment of the invention. It should be noted that any process descriptions or blocks in flow charts should be understood as representing modules, segments, portions of code, or steps that include one or more instructions for implementing specific logical functions in the process, and alternate implementations are included within the scope of the present invention in which functions may be executed out of order from that shown or discussed, including substantially concurrently or in reverse order, depending on the functionality involved, as would be understood by those reasonably skilled in the art of the present invention.

As is shown by block 402, a container 10 is provided having an opening, a plurality of fluid permeable sides 12, and a latch unit 18, moveably affixed to a first side 20 of the plurality of fluid permeable sides 12. A lid 16 is placed over the opening of the container 10 (block 404). The latch unit 18 is moved to a closed position (block 406). A locking mechanism 28 located within the latch unit 18 is manipulated to engage the first side 20 (block 408). Manipulation of the latch unit 18 may include compressing a compression-tension element, such as a spring or flexible material. A lid restraint 26 integral with the latch unit 18 is engaged with the lid 16 (block 410).

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

What is claimed is:

1. A container comprising:
   a plurality of sides, each side having a plurality of fluid permeable openings, wherein the plurality of sides form a partially enclosed unit;
   at least one lid;
   at least one latch unit movably attached to a first side of the plurality of sides at a proximate end of the latch unit;
   a lid restraint formed at a distal end of the latch unit whereby the lid restraint restrains the lid when engaged with the lid, wherein the lid restraint projects inwardly of an inside surface of the at least one latch unit to engage the lid; and
   at least one locking element formed along the latch unit for engagement with the first side, wherein engagement of the locking element with the first side limits the mobility of the latch unit.

2. The container of claim 1, further comprising at least one lock opening formed in the first side, sized to receive the locking element.

3. The container of claim 1, wherein the at least one lid is removably secured to a second side.

4. The container of claim 1, wherein the at least one lid is removably secured to a second side with a slidable engagement element.

5. The container of claim 1, wherein the at least one latch unit is integral with the first side.

6. The container of claim 1, wherein the proximate end of the at least one latch unit is pivotably attached to the first side, wherein the lid restraint formed at the distal end of the latch unit rotates to pivotally engage with the lid.

7. The container of claim 1, wherein the proximate end of the at least one latch unit is slidably attached to the first side.

8. The container of claim 1, wherein the at least one locking element further comprises at least one compression-tension system.

9. The container of claim 1, wherein the at least one locking element further comprises two locking elements located at symmetrically opposite positions on the latch unit.

10. The container of claim 1, wherein the at least one latch unit further comprises a plurality of locking elements.

11. The container of claim 1, wherein the at least one locking element is movable between at least a first position and a second position and further comprising a biasing mechanism, in mechanical communication with the locking element, biasing the locking element into the first position.

12. The container of claim 1, wherein the at least one latch unit further comprises a first latch unit and a second latch unit, the first latch unit movably attached to the first side and the second latch unit movable attached to a second side of the plurality of sides.

13. The container of claim 1, wherein the at least one latch includes a carrying handle disposed within the at least one latch unit.

14. The container of claim 1, wherein the lid further comprises a lid retainer area located on an edge of the lid, wherein the lid restraint restrains the lid when engaged with the lid by securing the lid retainer area directly between the lid restraint and at least one of the plurality of sides.

15. The container of claim 1, wherein the plurality of sides further comprises a second side positioned opposite the first side, wherein the second side has a receiving slot sized to receive a first edge of the lid therein.

16. The container of claim 15, wherein the first edge of the lid is positioned within the receiving slot when the at least one latch unit is engaged with the lid.

17. The container of claim 1, wherein the lid further comprises a retaining area formed proximate to an edge of the lid, wherein the retaining area at least partially extends below a planar top surface of the lid.

18. The container of claim 17, wherein the lid restraint formed at the distal end of the latch unit engages with the retaining area of the lid, wherein when the lid restraint is in an engaged position with the retaining area of the lid, the lid restraint is positioned below the planar top surface of the lid.

\* \* \* \* \*